US010966667B2

(12) United States Patent
Salah et al.

(10) Patent No.: US 10,966,667 B2
(45) Date of Patent: Apr. 6, 2021

(54) METHOD FOR PREDICTING A DENTAL SITUATION

(71) Applicant: DENTAL MONITORING, Paris (FR)

(72) Inventors: Philippe Salah, Paris (FR); William Ayache, Neuilly-sur-Seine (FR); Guillaume Ghyselinck, Cantin (FR); Laurent Debraux, Paris (FR); Louis Charles Roisin, Paris (FR); Thomas Pellissard, Clichy (FR)

(73) Assignee: DENTAL MONITORING, Paris (FR)

( * ) Notice: Subject to any disclaimer, the term of this patent is extended or adjusted under 35 U.S.C. 154(b) by 32 days.

(21) Appl. No.: 16/094,255

(22) PCT Filed: Apr. 21, 2017

(86) PCT No.: PCT/EP2017/059547
§ 371 (c)(1),
(2) Date: Nov. 9, 2018

(87) PCT Pub. No.: WO2017/182648
PCT Pub. Date: Oct. 26, 2017

(65) Prior Publication Data
US 2019/0125274 A1 May 2, 2019

(30) Foreign Application Priority Data

Apr. 22, 2016 (FR) ...................... 1653589

(51) Int. Cl.
A61B 5/00 (2006.01)
A61C 7/00 (2006.01)
(Continued)

(52) U.S. Cl.
CPC ............ *A61B 5/7275* (2013.01); *A61C 7/002* (2013.01); *G06T 7/0014* (2013.01); *G06T 17/00* (2013.01);
(Continued)

(58) Field of Classification Search
CPC ..... A61B 5/7275; A61B 6/466; A61B 5/0062; A61C 7/002; A61C 9/0053; A61C 9/0046;
(Continued)

(56) References Cited

U.S. PATENT DOCUMENTS 6,406,292 B1   6/2002 Chishti et al.
2004/0197727 A1   10/2004 Sachdeva et al.
(Continued)

FOREIGN PATENT DOCUMENTS

WO   2008149221 A1   12/2008
WO   2016135549 A1   9/2016

OTHER PUBLICATIONS

Corresponding International Application, Application No. PCT/EP2017/059547 Search Report, dated Jul. 10, 2017, 6 Pgs.

*Primary Examiner* — Jingge Wu
(74) *Attorney, Agent, or Firm* — Cooper Legal Group, LLC; Ronald M. Kachmarik

(57) ABSTRACT

A method for predicting a future dental situation for a patient. Acquiring historical data including at least: previous time point and context parameter values. Acquiring at a time point all the data related to the current dental situation, including at least: the current time point, context parameter values at the current time point, statistical analysis of the historical data and the current data, so as to predict, at a future time point, at least one future dental situation for the current patient. Depending on the future dental situation, (re)evaluation of the benefit of an orthodontic treatment. Steps may include creating a three-dimensional digital reference model, acquiring at least one two-dimensional image, analysing each updated image and creation, searching, for (Continued)

each updated image, and collecting data relative to the updated reference model and relative to the orthodontic appliance.

15 Claims, 5 Drawing Sheets

(51) Int. Cl.
| | |
|---|---|
| *G16H 30/40* | (2018.01) |
| *G16H 50/70* | (2018.01) |
| *G16H 50/50* | (2018.01) |
| *G16H 10/60* | (2018.01) |
| *G16H 50/20* | (2018.01) |
| *G06T 7/00* | (2017.01) |
| *G06T 17/00* | (2006.01) |

(52) U.S. Cl.
CPC ............ *G16H 10/60* (2018.01); *G16H 30/40* (2018.01); *G16H 50/20* (2018.01); *G16H 50/50* (2018.01); *G16H 50/70* (2018.01); *A61B 2503/06* (2013.01); *A61B 2503/08* (2013.01); *G06T 2207/30036* (2013.01); *G06T 2210/41* (2013.01); *G06T 2210/44* (2013.01)

(58) Field of Classification Search
CPC .... A61C 13/0004; G16H 50/50; G16H 10/60; G16H 30/40; G16H 50/20; C06T 7/0014; G06T 17/00; G06T 2207/30036; G06T 19/20
See application file for complete search history.

(56) References Cited

U.S. PATENT DOCUMENTS

| | | | |
|---|---|---|---|
| 2006/0153436 A1* | 7/2006 | Haras | A61B 6/466 382/131 |
| 2009/0191503 A1 | 7/2009 | Matov et al. | |
| 2014/0294273 A1* | 10/2014 | Jaisson | A61B 5/0035 382/131 |
| 2015/0227702 A1* | 8/2015 | Krishna | A61B 5/4094 705/2 |
| 2018/0042698 A1* | 2/2018 | Salah | A61B 5/0088 |
| 2018/0111320 A1* | 4/2018 | Zhao | B33Y 50/00 |
| 2018/0204332 A1* | 7/2018 | Salah | A61B 5/0062 |
| 2019/0125493 A1* | 5/2019 | Salah | G16H 50/20 |
| 2020/0067396 A1* | 2/2020 | Rubin | H02P 25/066 |

* cited by examiner

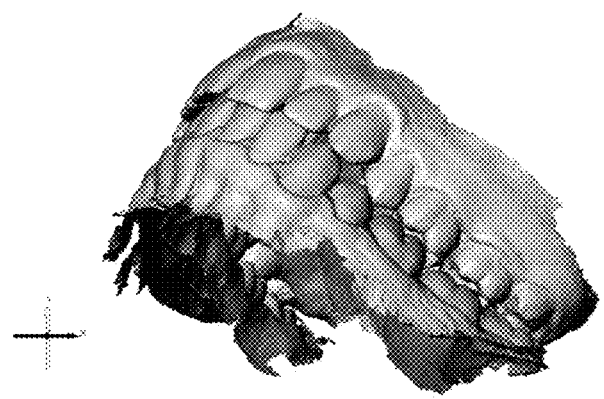
Fig.4
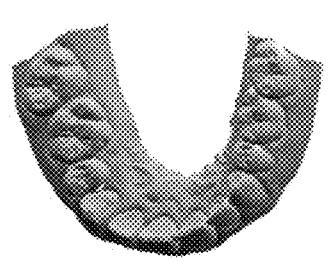 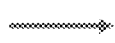 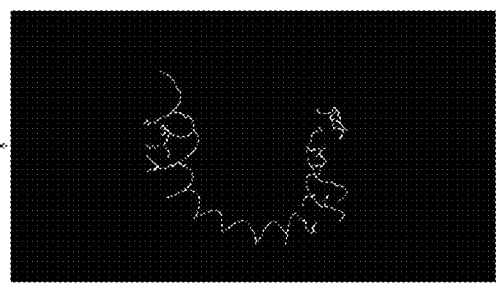
Fig. 5a                    Fig. 5b
                    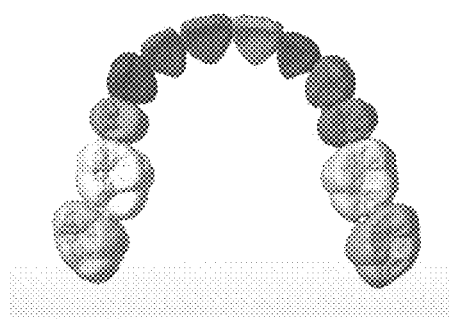
Fig. 5c                    Fig. 5d

METHOD FOR PREDICTING A DENTAL SITUATION

TECHNICAL FIELD

The present invention concerns a method for predicting a dental situation and a method for determining, according to said prediction, an orthodontic appliance intended to correct a malposition of a patient's teeth.

STATE OF THE ART

Conventionally, at the start of an orthodontic treatment, the orthodontist determines the position of the teeth that they want to obtain from the treatment, called "final setup". The final setup may be defined by using an impression or from a three-dimensional scan of the patient's teeth. Then the orthodontist creates a suitable orthodontic appliance for this treatment.

The orthodontic appliance may conventionally be an appliance with attachments having a metal orthodontic archwire attached to the teeth.

Alternatively, the orthodontic appliance may be an aligner. An orthodontic aligner is conventionally in the form of a single-piece removable appliance, conventionally of a transparent polymer material, that has a moulded trough so that several teeth of an arch, usually all the teeth of an arch, may be held there. The shape of the trough is designed to hold the aligner in position on the teeth, while exerting a corrective action on the position of certain teeth.

Treatment with aligners is advantageously less restrictive for the patient. In particular, the number of orthodontist appointments is limited. Moreover, the pain is less than with a metal orthodontal archwire attached to the teeth.

The orthodontic aligner market is therefore growing.

If the orthodontic appliance is an aligner, conventionally, at the start of treatment, the shapes that the different aligners must have at different times during the treatment are determined. The desired position of the teeth of each of these times is called "intermediate setup".

The orthodontist then has all the corresponding aligners made. The number of aligners is conventionally around twenty. At the predetermined times, the patient changes aligner.

Regardless of the orthodontic appliance used, at regular intervals, the patient goes to the orthodontist for a visual checkup. Depending on their diagnosis, the orthodontist may change the orthodontic appliance.

For example, if the orthodontic appliance is an appliance with a metal orthodontic archwire attached to the teeth, the orthodontist may modify the tension exerted by the orthodontic archwire. If necessary, they may also have a new, better adjusted orthodontic appliance made.

If the orthodontic appliance is an aligner, the orthodontist may make a new impression of the teeth, or, equivalently, a new three-dimensional scan of the teeth, then order a new series of aligners. On average, the number of aligners finally created is around 45, instead of the 20 aligners conventionally planned at the start of treatment.

The need to go to the orthodontist for a checkup is an imposition for the patient. The increasing number of checkups may also undermine the patient's confidence in their orthodontist. Finally, this leads to additional costs.

There is therefore a need to limit the number of checkups at the orthodontist.

Moreover, there is an ongoing need to accelerate orthodontic treatments.

Furthermore, beyond any orthodontal treatment, there is a need to better anticipate the evolution of the position of patient cs' teeth, in particular during growth of the teeth in children or aging in the elderly. In the elderly, aging especially leads to advancement of the teeth.

One objective of the invention is to at least partially meet these needs.

SUMMARY OF THE INVENTION

The invention proposes a method for predicting a future dental situation for a patient, called "current patient", in particular for a current patient wearing an orthodontic appliance, called "current orthodontic appliance", intended to correct a malposition of their teeth, said prediction method including the following steps:

1) acquisition of data, called "historical data", relative to past dental situations, called "previous dental situations", each experienced at a time called "previous time" by a patient called "previous patient", the previous patient being able, in particular, to undergo an orthodontic treatment called "previous orthodontic treatment", during which they are provided with orthodontic appliance called "previous orthodontic appliance", all the historical data relative to a previous dental situation including at least:
   said previous time point;
   context parameter values at said previous time point, the context parameters including:
      preferably, if the previous patient has a previous orthodontic appliance,
         parameters of said previous orthodontic appliance, in particular relative to the class and/or conformation of the previous orthodontic appliance;
         preferably, parameters on the previous orthodontic treatment environment to which the previous dental situation relates, such as a pain coefficient and/or a cost and/or a duration and/or a number of orthodontist appointments and/or a probability of success, associated with said previous orthodontic treatment;
      tooth positioning parameters of said previous patient;
      preferably anatomical parameters other than tooth positioning, such as the arrangement and/or structure of bony tissue (especially the jaws) and/or alveolar tissue and/or soft tissue (especially the gums and/or frenulum and/or tongue and/or cheeks), of the previous patient;
      preferably, functional parameters of the previous patient, in particular neurofunctional parameters, such as ease in breathing, swallowing or shutting the mouth;
      preferably, the age and/or sex and/or an identifier of said previous patient;

2) acquisition at a time point, called "current time point", of data relative to a dental situation experienced by said current patient, called "current dental situation", all the data related to said current dental situation, called "current data", including at least:
   preferably, said current time point;
   context parameter values at said current time point, the context parameters including:
      preferably, if the current patient has a current orthodontic appliance, parameters of said current orthodontic appliance, in particular relative to the class and/or conformation of the current orthodontic appliance;

preferably, parameters on the current orthodontic treatment environment to which the current dental situation relates, called "current orthodontic treatment", such as a pain coefficient and/or a cost and/or a duration and/or a number of orthodontist appointments and/or a probability of success, associated with the current orthodontic treatment;

tooth positioning parameters of said current patient;

preferably anatomical parameters other than tooth positioning, such as the arrangement and/or structure of bony tissue (especially the jaws) and/or alveolar tissue and/or soft tissue (especially the gums and/or frenulum and/or tongue and/or cheeks), of the current patient;

preferably, functional parameters of the current patient, in particular neurofunctional parameters, such as ease in breathing, swallowing or shutting the mouth;

preferably, the age and/or sex and/or an identifier of said current patient;

3) statistical analysis of said historical data and said current data, so as to predict, at at least one future time point, at least one future dental situation for the current patient;

4) depending on said future dental situation, evaluation of the benefit of an orthodontic treatment for the current patient or, if the current patient has a current orthodontic appliance, reevaluation of the current orthodontic treatment, preferably by an orthodontist and, depending on said reevaluation, possible change in the orthodontic treatment of the current patient, for example, modification or change of the current orthodontic appliance and/or change of an orthodontist appointment schedule.

The ability to predict future dental situations is a considerable advantage relative to the situation prior to the invention.

Generally, it actually becomes possible to predict an evolution of the position of the teeth, whether or not in the context of orthodontic treatment. For example, it becomes possible to predict how a child's teeth will move as they grow, which makes it possible to act very early to correct an unfavorable situation.

Likewise, teeth have a tendency to move, especially as the patient ages. Thanks to the invention, it becomes possible to predict this movement, which makes it possible to act very early to correct an unfavorable situation.

The ability to predict future dental situations is especially a considerable advantage when the current patient is undergoing orthodontic treatment.

Indeed, prior to the present invention, during a checkup, the orthodontist could only perceive the most visible anomalies, for example a significant detachment of the aligner worn in certain areas. Their ability to anticipate was therefore limited. Moreover, the orthodontist could misinterpret a situation. For example, they could believe that a detachment of an aligner was an anomaly, while this detachment was only temporary, or would remain limited.

Advantageously, the prediction made by the procedure according to the invention allows them to understand a future situation that visual observation alone does not permit conceiving of. They therefore may, for example, choose not to change the current orthodontic appliance even if they perceive a detachment. Conversely, they may change the current orthodontic appliance even if they do not perceive a detachment, or a very slight detachment.

As will be seen in detail in the rest of the description, the efficacy of the orthodontic treatment is thereby considerably improved.

The current orthodontic appliance may be an aligner. A method according to the invention is particularly well suited to determine the most suitable times for changing the aligner worn by a current patient.

At step 3), the following is preferably determined, for at least one, preferably for each said future dental situation, and/or for at least one, preferably for each said future time point, if the current patient has a current orthodontic appliance, values, at said future time point, of parameters of said current orthodontic appliance; and/or values of tooth positioning parameters of the current patient at said future time point (in particular at an objective future time point); and/or preferably, a difference of the value of one or more tooth positioning parameters of the current patient from the value of said positioning parameter or parameters in a dental situation constituting an objective at said future time point; and/or a cost for said future dental situation to be achieved; and/or a pain coefficient for said future dental situation to be achieved; and/or a probability that the predictions relating to the parameters of the current dental appliance if the current patient has such an appliance and/or the tooth positioning parameters of said current patient, and/or said cost and/or said pain coefficient will comply with reality.

Preferably, at step 3), several future dental situations are determined, for a single future time point, and/or at least one future dental situation, for several different future time points.

Preferably, several said statistical analyses are carried out, each time modifying said future time point, so as to predict future dental situations up to an objective future time point, for example up to an intermediate or final setup. This cycling makes it possible to predict an evolution of the position of the teeth and/or a "potential orthodontic treatment" up to the objective future time point.

Preferably, one or more potential orthodontic treatments are determined to obtain, at an objective future time point, a determined objective future dental situation or an objective future dental situation being within a determined range of dental situations.

Preferably, potential first and second orthodontic treatments are determined which lead, at said objective future time point, for at least one tooth positioning parameter of the current patient, to extreme dental situations. The "extreme" situations correspond to the minimum and maximum limits for said positioning parameter, i.e. to limits within and beyond which, respectively, the dental situation at said objective future time point is considered unacceptable.

Represented on the same graph, the curves showing the evolution over time of said positioning parameter value for these potential first and second orthodontic treatments define a surface, called "biozone" which, advantageously, makes it possible to easily identify an abnormal shift of the tooth positioning. It is sufficient, at any given time, to measure said positioning parameter value and check whether, at this time point, it is within the biozone.

The initial time point of the potential orthodontic treatment or treatments may be, in particular, the current time point or an initial time point corresponding to the start of a current orthodontic treatment with an orthodontic appliance worn by the current patient.

Preferably, several potential orthodontic treatments are determined by changing at least one constraint each time.

Advantageously, the orthodontist may therefore evaluate the impact of a change in a constraint. For example, they may change the constraint of the metal archwire diameter and observe the effect of this change on the potential orthodontic treatment.

Preferably, the method includes an operation of optimizing the constraints depending on at least one optimization criterion, an operation in which a succession of statistical analyses are implemented by changing one or more of said constraints each time for a single future time point, until an optimal dental situation is found with regard to the optimization criterion, following at least one optimization rule.

Preferably, by implementing a succession of statistical analyses, several potential orthodontic treatments are established, corresponding to the application of different constraints, until a potential optimal orthodontic treatment is found with regard to the optimization criterion following at least one optimization rule.

Preferably, the optimization criterion is chosen from the group made up of a pain coefficient, a cost, a difference from a desired value for a positioning parameter, a duration, a number of orthodontist appointments, a number of aligners, a probability of success, or a combination of these criteria, each criterion being able to be associated with the current orthodontic treatment or a dental situation of said current orthodontic treatment, for example said current dental situation or at a future objective time point.

Definitions

A "current patient" is a person for whom the method according to the invention is implemented to predict a future dental situation, independently of whether or not this person has a tooth malposition. The patient is called "current" for purposes of clarity, to distinguish them from a "previous" patient.

"Dental situation" means a situation relative to a position of the teeth.

A "category" of patients groups all the patients according to physiological data, for example, groups all the patients in a particular age bracket and/or of the same sex.

A "class" of orthodontic appliances defines a set of comparable orthodontic appliances. For example, a class of orthodontic appliances may group all the orthodontic appliances that are active aligners of a same material, or all the orthodontic appliances with attachments provided to a single metal archwire.

The "context parameters" are the parameters useful for evaluating a dental situation. They notably include the tooth positioning parameters of the patient considered and, if applicable, the parameters of the orthodontic appliance considered.

The "orthodontic appliance parameters" include intrinsic parameters such as the material(s) that make up said orthodontic appliance or the rest shape parameters, for example the shape of an aligner or the diameter of an orthodontic archwire. They also include application parameters.

In one embodiment, the parameters of the orthodontic appliance are general parameters that identify the class of the orthodontic appliance.

A "shape parameter" is a useful parameter for determining the shape of an orthodontic appliance. For example, x, y and z are shape parameters in an Oxyz Cartesian coordinate system. The values of these shape parameters make it possible to define the position of a point of the orthodontic appliance in space, preferably a point of the surface of the orthodontic appliance. A shape parameter may also be a diameter of an orthodontic archwire, a material thickness or a dimension, for example.

An "application parameter" is a useful parameter for determining how the orthodontic appliance operates in the dental situation considered. The position of the attachment points for the orthodontic archwire onto the teeth or the tension of the orthodontic archwire are examples of application parameters. The duration for which the orthodontic appliance has already been worn at the time point considered is also an application parameter.

A "positioning parameter" is a useful parameter for determining the position of a tooth. For example, the x-axis, the y-axis, and the z-axis, are positioning parameters in an Oxyz Cartesian coordinate system. The radial coordinate, often denoted r or $\rho$, and called the radius, the angular coordinate, also called polar angle or azimuth, and often denoted t or $\theta$, and the height, often denoted h, are positioning references in a cylindrical coordinate system. The values of these positioning parameters make it possible to define the position of a point in space.

The parameters used to determine the shape of an orthodontic appliance may be identical or different from the parameters used to determine the position of the teeth. For purposes of clarity, these parameters are designated differently, by "shape parameters" and "positioning parameters", respectively.

The "constraints" are parameters whose values are not free. The following are distinguished:
  the "nonadjustable" constraints, in particular the tooth positioning parameters of the current patient at the current time point or the parameters relative to the current patient, such as age or sex.
  the "adjustable" constraints, for which the orthodontist or current patient may set ranges of variation, at the current time point and/or at one or more future time points.

A range of acceptable positions for the current patient's teeth at a future time point, a maximum treatment cost, a maximum pain coefficient during the treatment or a mean pain coefficient during the current orthodontic treatment are examples of adjustable constraints.

In particular, when seeking a better suited orthodontic appliance for the orthodontic treatment, by modifying or switching out the current orthodontic appliance, the current orthodontic appliance parameters, for example the shape of the aligner, may also be adjustable constraints.

The "acquisition conditions" for an image specify the position and orientation in space of an image acquisition device relative to the patient's teeth or a model of the patient's teeth, and preferably the calibration of this image acquisition device. Acquisition conditions are called "virtual" when they correspond to a simulation in which the acquisition device would be in said acquisition conditions (theoretical positioning and preferably theoretical calibration for the acquisition appliance).

A "setup" conventionally means a position of the teeth that the treatment aims to achieve at a treatment time point, in particular at the end of treatment ("final setup") or at a predetermined intermediate treatment stage ("intermediate setup"), for example at a planned time point to change the aligner or change the tension of the orthodontic archwire. The "calibration" of an acquisition device consists of all the calibration parameter values. A "calibration parameter" is a parameter intrinsic to the acquisition device (unlike its position and orientation), the value of which influences the image acquired. Preferably, calibration parameters are chosen from the group made up of the aperture, exposure time, focal length and sensitivity.

"Image" means a two-dimensional image, such as a photograph. An image is formed of pixels.

A "preview" image is the image that the acquisition device may record at a given time point. For a camera or a telephone, it is the image that appears on the screen when the photo or video acquisition device is in operation.

"Discriminant information" is characteristic information that may be extracted from an image ("image feature"), conventionally by a computer processing of this image.

Discriminant information may have a variable number of values. For example, contour information may be equal to 1 or 0 depending on whether or not a pixel belongs to a contour. Brightness information may take on a large number of values. Image processing makes it possible to extract and quantify discriminant information.

"Metaheuristic" methods are known optimization methods. They are preferably chosen from the group made up of
- evolutionary algorithms, preferably chosen from: evolution strategies, genetic algorithms, differential evolution algorithms, distribution estimation algorithms, artificial immune systems, Shuffled Complex Evolution path recomposition, simulated annealing, ant colony algorithms, particle swarm optimization algorithms, tabu search, and the GRASP method;
- the kangaroo algorithm,
- the Davidon-Fletcher-Powell method,
- the sound effects method,
- stochastic tunneling,
- random restart hill-climbing,
- the cross-entropy method, and
- hybrid methods between the metaheuristic methods cited above.

"Comprising", "including" or "presenting" should be interpreted in an unrestricted manner, unless otherwise indicated.

BRIEF DESCRIPTION OF THE FIGURES

Other characteristics and advantages of the invention will appear upon reading the detailed description that follows and examining the attached drawing, in which:

FIG. 4 shows an example initial reference model, FIG. 5 (5a-5d) illustrates processing to determine the tooth models in a reference model, FIG. 6 (6a-6d) illustrates the acquisition of an updated image by means of a retractor, an operation of cutting of this image, and the processing of an updated image making it possible to determine the contour of the teeth, FIG. 7 schematically illustrates the relative position of reference marks 12 of a retractor 10 on updated images $14_1$ and $14_2$, along the directions of observation shown by the dashed lines.

DETAILED DESCRIPTION

Figure 1:
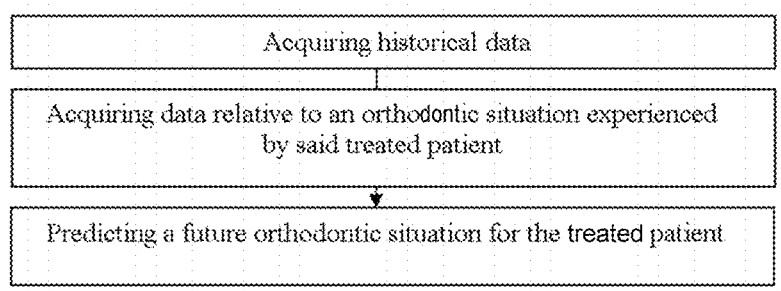
FIG. 1 is a flowchart illustrating the implementation of a prediction method according to the invention, FIGS. 2 (2a to 2e) shows examples of graphic representations providing predictions obtained by the implementation of a method according to the invention for the value of a tooth positioning parameter, as a function of time.

Step 1) is a step of acquiring historical data. It must start before step 3), but, preferably, continues during and after step 3).

Each previous situation corresponds to a situation has which a previous patient been in, and for which historical data have been identified.

The number of previous situations for which historical data are acquired is preferably more than 1,000, preferably more than 10,000, preferably more than 100,000, preferably more than 500,000.

The precision of the statistical analysis is thereby improved.

The previous situations may concern different classes of orthodontic appliances.

The number of previous situations relative to a single class of orthodontic appliances is preferably more than 1,000, preferably more than 10,000, preferably more than 100,000, preferably more than 500,000.

The number of previous situations relative to a single category of patients is preferably more than 1,000, preferably more than 10,000, preferably more than 100,000, preferably more than 500,000.

The previous situations preferably concern more than 100, more than 1,000, more than 10,000, more than 50,000 different patients.

Preferably, all the historical data are recorded in a computer database.

Of course, the current patient may have experienced previous situations, and therefore themselves been a "previous patient".

Step 2) is a step of collecting current data relating to the current situation experienced by the current patient and that are relevant for the statistical analysis of step 3).

The current data preferably make it possible to determine the category to which the current patient belongs.

If the current patient wears a current orthodontic appliance, the current data make it possible to determine parameters of this appliance, but also, preferably, the class of this appliance.

At step 1) and/or step 2), historical or current data acquisition, respectively, may be done by any means. It may particularly result from the implementation of a data acquisition method including the following steps:
a) creating a three-dimensional digital reference model of at least one part of an arch, preferably at least one arch of a patient (current or previous), or "initial reference model" and, preferably, for each tooth, defining, from the initial reference model, a three-dimensional digital reference model of said tooth, or "tooth model";
b) acquiring at least one two-dimensional image of the patient's arches, called "updated image" under actual acquisition conditions;
c) analysing each updated image and creation, for each updated image, of an updated map relating to discriminant information;
d) optionally, determining, for each updated image, virtual acquisition conditions roughly approximating said actual acquisition conditions;
e) searching, for each updated image, by means of the updated map, by deformation of the initial reference model, for an updated reference model corresponding to the positioning of the teeth during the acquisition of the updated image, the search being preferably carried out by means of a metaheuristic method, preferably an evolutionary method, preferably by simulated annealing, and f) collecting data relating to the updated reference model and preferably, if the patient wears an orthodontic appliance, relating to said orthodontic appliance.

Depending on whether this method is implemented at step 1) or step 2), these collected data will be historical or current data, respectively.

The creation of the updated reference model is advantageously possible without any special precautions, especially since the actual positioning of the teeth is measured with an updated reference model that results from a deformation of the initial reference model so that it corresponds to the observations provided by the updated images, i.e. so that the updated images are views of the deformed initial reference model.

Figure 3:
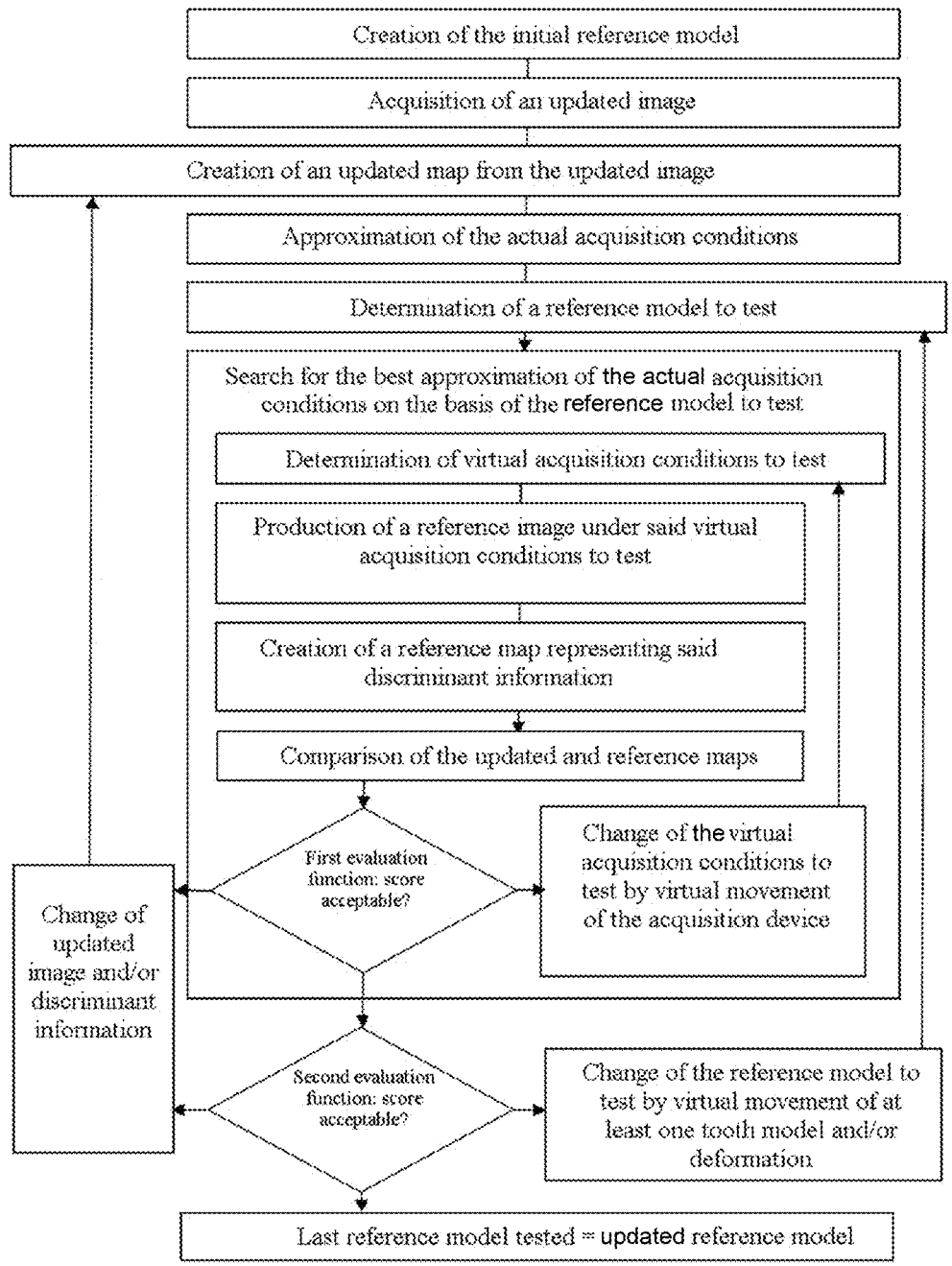
FIG. 3 is a flowchart illustrating the implementation of a method for easily acquiring historical or current data.

Such a data acquisition method, illustrated in FIG. 3, thus makes it possible, from one or more simple images of the teeth, taken without precise pre-positioning of the teeth with respect to the image acquisition device, for example from a photograph taken by the patient, to accurately assess the position of the teeth at the time of step b). This assessment may be done remotely, from simple photographs taken by a cell phone, so that the patient does not need to go anywhere, in particular to the orthodontist.

If the patient wears an orthodontic appliance, this assessment advantageously makes it possible to acquire lots of data to establish correlations between parameters of the orthodontic appliance, its behavior and configurations of the teeth.

At step a), an initial reference model of the patient's arches, or a part of the patient's arches, is created with a 3D scanner. Such a model, called "3D", illustrated in FIG. 4, may be observed from any angle.

The initial reference model may be prepared from measurements made on the patient's teeth or on a physical model of their teeth, for example a plaster model.

In the initial reference model, a part that corresponds to one tooth, or "tooth model" is defined by a gingival border that may be broken down into an inner gingival border (on the inside of the mouth relative to the tooth), an outer border (oriented toward the outside of the mouth relative to the tooth) and two lateral gingival borders.

At step b), an updated image of a part of the arch, an arch, or arches is taken by means of an image acquisition device, preferably a cell phone.

Figure 6A:
Figure 6B:
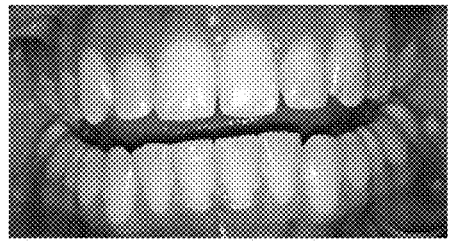
Figure 6C:
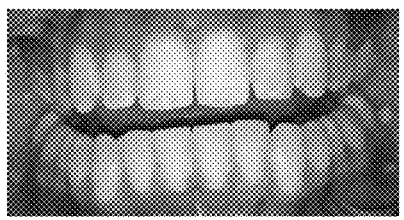
Figure 6D:
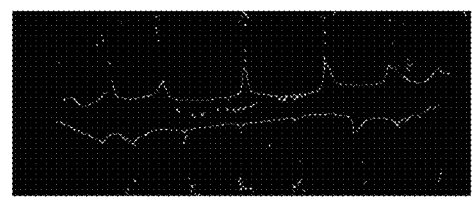

Preferably, a dental retractor is used in step b), as shown in FIG. 6a. The retractor conventionally includes a support provided with a rim extending around an opening and arranged so that the patient's lips may rest therein, leaving the patient's teeth visible through said opening.

At step c), each updated image is analyzed so as to create, for each updated image, an updated map relating to at least some discriminant information.

An updated map shows discriminant information in the frame of reference of the updated image. For example, FIG. 5b is an updated map relative to the contour of the teeth obtained from the updated image of FIG. 5a.

The discriminant information is preferably chosen from the group made up of contour information, color information, density information, distance information, brightness information, saturation information, information regarding reflections and combinations of these pieces of information.

The skilled person knows how to process an updated image to show discriminant information.

At optional step d), the actual acquisition conditions for step b) are roughly determined. In other words, at least the relative position of the image acquisition device at the time it takes the updated image is determined (position of the acquisition device in space and orientation of this device). Step d) advantageously makes it possible to limit the number of tests on virtual acquisition conditions during step e) and therefore permits considerably accelerating step e).

Preferably, one or more heuristic rules are used. For example, preferably, virtual acquisition conditions likely to be tested in step e) are excluded, the conditions that correspond to a position of the image acquisition device behind the teeth or at a distance from the teeth greater than 1 m.

Figure 7:
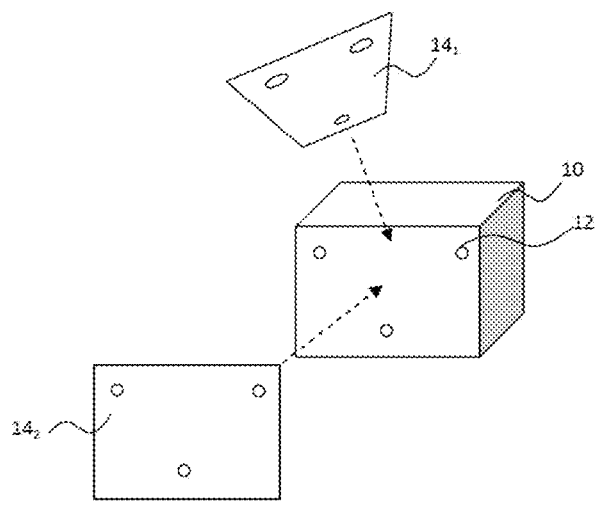
Figure 8:
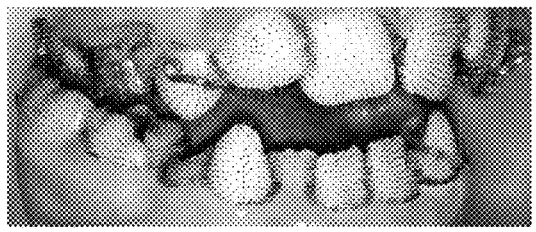
FIG. 8 shows, in an acquired image, a reference map established for reflection information.

In one preferred embodiment, as illustrated in FIG. 7, reference marks shown are used in the updated image, and, in particular reference marks 12 of the retractor, to determine an essentially conical region of space defining virtual acquisition conditions likely to be tested in step e), or "test cone".

Specifically, there are preferably at least three reference marks 12 not aligned on the retractor 10, and their relative positions on the retractor are precisely measured.

The reference marks are then identified on the updated image, as described previously. Simple trigonometric calculations make it possible to approximately determine the direction according to which the updated image was taken.

Step d) only allows a rough assessment of the actual acquisition conditions. Step d) nevertheless makes it possible to determine a restricted set of virtual acquisition conditions likely to correspond to the actual acquisition conditions, and, in this set, virtual acquisition conditions constituting the best starting point for step e) described below.

The objective of step e) is to modify the initial reference model in order to obtain an updated reference model that corresponds to the updated image. Ideally, the updated reference model is therefore a three-dimensional digital reference model from which the updated image could have been taken if this model was actual.

Therefore, a succession of reference models "to test" are tested, the choice of a reference model to test being preferably dependent on the degree of correspondence of the reference models "to test" previously tested with the updated image. This choice is preferably made by following a known optimization process, in particular chosen from among metaheuristic, preferably evolutionary, optimization processes, in particular from among simulated annealing processes.

Preferably, step e) includes
a first optimization operation to search for virtual acquisition conditions best corresponding to the actual acquisition conditions in a reference model to test determined from an initial reference model, and
a second optimization operation to search, by testing a plurality of said reference models to test, for the reference model best corresponding to the positioning of the patient's teeth during the acquisition of the updated image at step b).

Preferably, a first optimization operation is conducted for each test of a reference model to test during the second optimization operation.

Preferably, the first optimization operation and/or the second optimization operation, preferably the first optimization operation and the second optimization operation implement a metaheuristic, preferably evolutionary, method, preferably simulated annealing.

Preferably, step e) includes the following steps:
- e1) defining a reference model to test as being the initial reference model, then
- e2) following the next steps, testing virtual acquisition conditions with the reference model to test in order to finely approximate said actual acquisition conditions;
  - e21) determining virtual acquisition conditions to test;
  - e22) creating a two-dimensional reference image of the reference model to test under said virtual acquisition conditions to test;
  - e23) processing the reference image to create at least one reference map representing, at least partially, said discriminant information;
  - e24) comparing the updated and reference maps so as to determine a value for a first evaluation function, said value for the first evaluation function depending on the differences between said updated and reference maps and corresponding to a decision to continue or to stop the search for virtual acquisition conditions approximating said actual acquisition conditions with more accuracy than said virtual acquisition conditions to test determined at the last occurrence of step e21);
  - e25) if said value for the first evaluation function corresponds to a decision to continue said search, modifying the virtual acquisition conditions to test, then resuming at step e22);
- e3) determining a value for a second evaluation function, said value for the second evaluation function depending on the differences between the updated and reference maps under the virtual acquisition conditions best approximating said actual acquisition conditions and resulting from the last occurrence of step e2), said value for the second evaluation function corresponding to a decision to continue or to stop the search for a reference model approximating the positioning of the teeth during the acquisition of the updated image with more accuracy than said reference model to test used at the last occurrence of step e2), and if said value for the second evaluation function corresponds to a decision to continue said search, modifying the reference model to test by moving one or more tooth models, then resuming at step e2).

At step e1), it is determined that the reference model to test is the initial reference model during the first execution of step e2).

In step e2), virtual acquisition conditions to test are initially determined, i.e. a virtual position and orientation likely to correspond to the actual position and orientation of the acquisition device when capturing the updated image, but also, preferably, a virtual calibration likely to correspond to the actual calibration of the acquisition device when capturing the updated image.

The image acquisition device is then virtually configured under the virtual acquisition conditions to test so as to acquire a reference image of the reference model to test under these virtual acquisition conditions to test. The reference image therefore corresponds to the image that the image acquisition device would have taken if it had been positioned, relative to the reference model to test, and optionally calibrated, under the virtual acquisition conditions to test (step e22)).

If the updated image was taken while the position of the teeth was exactly the one in the reference model to test, and if the virtual acquisition conditions are exactly the actual acquisition conditions, the reference image may therefore be exactly superposed on the updated image. The differences between the updated image and the reference image result from errors in the evaluation of the virtual acquisition conditions (if they do not exactly correspond to the actual acquisition conditions) and movements of the teeth between step b) and the reference model to test.

To compare the updated and reference images, the discriminant information in these two images is compared. More precisely, a reference map is created from the reference image representing the discriminant information (step e23)).

The updated and reference maps, both relating to the same discriminant information, are then compared and the difference between these two maps is evaluated with a score. For example, if the discriminant information is the tooth contour, the mean distance between the points of the tooth contour that appears on the reference image may be compared with the corresponding points of the contour that appears on the updated image, the score being higher the shorter this distance.

Preferably, the virtual acquisition conditions include the calibration parameters of the acquisition device. The score is higher the closer the calibration parameter values tested are to the calibration parameter values of the acquisition device used in step b). For example, if the aperture tested is far from the one of the acquisition device used in step b), the reference image has blurry regions and sharp regions that do not correspond to the blurry regions and sharp regions of the updated image. If the discriminant information is the tooth contour, the updated and reference maps will therefore not show the same contours and the score will be low.

The score may, for example, be a correlation coefficient.

The score is then evaluated by means of a first evaluation function. The first evaluation function makes it possible to decide whether the cycling in step e2) should be continued or stopped. The first evaluation function may be, for example, equal to 0 if the cycling should be stopped or equal to 1 if the cycling should be continued.

The value of the first evaluation function may depend on the score attained. For example, it may be decided to continue the cycling in step e2) if the score does not exceed a first limit. For example, if an exact correspondence between the updated and reference images leads to a score of 100%, the first limit may be, for example, 95%. Of course, the higher the first limit, the better the precision of the evaluation of the virtual acquisition conditions if the score exceeds this first limit.

The value of the first evaluation function may also depend on the scores obtained with virtual acquisition conditions tested previously.

The value of the first evaluation function may also depend on random parameters and/or the number of cycles of step e2) already conducted.

In particular, it is possible that despite the repetition of the cycles, it is not possible to find virtual acquisition conditions that are sufficiently close to the actual acquisition conditions for the score to reach said first limit. The first evaluation function may therefore lead to the decision to stop the cycling even though the best score obtained did not reach said first limit. This decision may result, for example, from a number of cycles greater than a predetermined maximum number.

A random parameter in the first evaluation function may also allow tests of new virtual acquisition conditions to be continued, even though the score appears satisfactory.

The evaluation functions conventionally used in meta-heuristic, preferably evolutionary, optimization processes, in particular in simulated annealing processes, may be used for the second evaluation function.

If the value of the first evaluation function indicates that it is decided to continue the cycling in step e2), the virtual acquisition conditions tested (step e25)) are modified and a cycle is started again (step e2)) consisting of making a reference image and a reference map, and then comparing this reference map with the updated map to determine a score.

The modification of the virtual acquisition conditions corresponds to a virtual movement in space and/or a change in the orientation and/or, preferably, a change in the calibration of the acquisition device. This change may be random, as long as the new virtual acquisition conditions to test still belong to the set determined in step d). The change is preferably guided by heuristic rules, for example by favoring the changes that, according to an analysis of the previous scores obtained, appear the most favorable for increasing the score.

The cycling in e2) is continued until the value of the first evaluation function indicates that it is decided to leave this cycling and continue to step e3), for example if the score reaches or exceeds said first limit.

The virtual acquisition conditions in step e2) are preferably optimized by using a metaheuristic, preferably evolutionary, method, preferably a simulated annealing algorithm. Such an algorithm is well known for nonlinear optimization.

If the cycling was left in step e2), without being able to obtain a satisfactory score, for example without the score being able to reach said first limit, the process may be stopped (failure situation) or resumed in step c) with new discriminant information and/or with a new updated image. The process may also be continued with the virtual acquisition conditions corresponding to the best score attained. A warning may be emitted in order to inform the user of the error in the result.

If the cycling was left in step e2) with a satisfactory score being able to be obtained, for example because the score reached or even exceeded said first limit, the virtual acquisition conditions essentially correspond to the actual acquisition conditions.

Preferably, the virtual acquisition conditions include the calibration parameters of the acquisition device. The process conducted therefore makes it possible to evaluate the values of these parameters without needing to know the nature or settings of the acquisition device. Step b) may therefore, be conducted with no special precautions, for example by the patient themselves using their cell phone.

Moreover, the actual calibration is sought by comparing an updated image with views of an initial reference model under virtual acquisition conditions that are tested. Advantageously, it does not require the updated image to show a calibration gauge, that is to say a gauge whose characteristics are precisely known, to determine the calibration of the acquisition device.

The updated images are not used to create a totally new updated three-dimensional model, rather only to change the very precise initial reference model. A totally new updated three-dimensional model created from simple photographs taken with no special precautions would be in particular too imprecise for a comparison with the initial reference model to be able to lead to conclusions on tooth movement.

Differences may exist between the determined virtual acquisition conditions and the actual acquisition conditions, in particular if the teeth move between steps a) and b). The correlation between the updated and reference images may then still be improved by resuming step e2), the reference model to test being then modified by moving one or more tooth models (step e3)).

The search for the reference model optimally approximating the positioning of the teeth during the acquisition of the updated image may be performed like the search for the virtual acquisition conditions best approximating the actual acquisition conditions (step e2)).

In particular, the score is evaluated by means of a second evaluation function. The second evaluation function makes it possible to decide whether the cycling in steps e2) and e3) should be continued or stopped. The second evaluation function may be, for example, equal to 0 if the cycling should be stopped or equal to 1 if the cycling should be continued.

The value of the second evaluation function preferably depends on the best score obtained with the reference model to test, that is to say the differences between the updated and reference maps, under the virtual acquisition conditions best approximating said actual acquisition conditions.

The value of the second evaluation function may also depend on the best score obtained with one or more reference models tested previously.

For example, it may be decided to continue the cycling if the score does not exceed a second minimum limit. The value of the second evaluation function may also depend on random parameters and/or the number of cycles of steps e2) and e3) already conducted.

The evaluation functions conventionally used in nietaheuristic, preferably evolutionary, optimization processes, in particular in simulated annealing processes, may be used for the second evaluation function.

If the value of the second evaluation function indicates that it is decided to continue the cycling in steps e2) and e3), the reference model to test is modified and a cycle is started again (steps e2) and e3)) with the new reference model to test.

The change in the reference model to test corresponds to a movement of one or more tooth models. This change may be random. The change is preferably guided by heuristic rules, for example by favoring the changes that, according to an analysis of the previous scores obtained, appear the most favorable for increasing the score.

Preferably, the movement of a tooth model is sought that has the greatest impact on the score, the reference model to test is modified by moving this tooth model, then the cycling in steps e2) and e3) is continued so as to optimize the score. Then the model with the greatest impact on improving the score can be sought among the other tooth models, and the optimal movement of this other tooth model on the score can be sought again. This may be continued for each tooth model.

Next, it is possible to resume a cycle on all the tooth models and continue until a score higher than the second limit is obtained. Of course, other strategies may be used to move one or more tooth models in the reference model to test and search for the maximum score.

The cycling in steps e2) and e3) is continued until this value of second evaluation function indicates that it is decided to leave the cycling and continue to step f), for example if the score reaches or exceeds said second limit.

A reference model with cycling in steps e2) and e3) to search for the tooth model positions that optimize the score is preferably sought by using a metaheuristic, preferably evolutionary, method, preferably a simulated annealing algorithm. Such an algorithm is well known for nonlinear optimization.

If the cycling was left in steps e2) and e3), without being able to obtain a satisfactory score, for example without the score being able to reach said second limit, the process may be stopped (failure situation) or resumed in step c) with new discriminant information and/or with a new updated image.

If it is decided to restart the process in step c) from different discriminant information and/or another updated image because the first limit or the second limit has not been reached, the choice of the new discriminant information and/or the new updated image may depend on the scores obtained previously, in order to favor the discriminant information and/or the updated image which, in view of these scores, appear the most promising.

New discriminant information, obtained, for example, by combination of other discriminant information already tested, may be used. If applicable, it may also be necessary to acquire one or more new updated images. Preferably, indications are provided to guide the positioning of the acquisition device for the capture of this new updated image. For example, the patient may be told that they should take a photo of the right-hand part of their lower arch.

If the cycling was left in steps e2) and e3) without being able to obtain a satisfactory score, a warning may be issued in order to inform the user of the error in the result.

If the cycling was left in steps e2) and e3) with a satisfactory score being able to be obtained, for example because the score reached or even exceeded said second limit, the virtual acquisition conditions essentially correspond to the actual acquisition conditions and tooth models in the reference model obtained (called "updated reference model") are essentially in the position of the patient's teeth at the time of step b).

The cycling in steps e2 and e3) advantageously makes it possible to improve the evaluation of the acquisition device calibration parameters in step b).

After step e), the updated reference model essentially corresponds to the updated image. It is therefore possible to take precise measurements on the positioning of the teeth and/or the shape of the orthodontic appliance in order to acquire historical or current data.

Steps a) to e) may include one or more characteristics of the corresponding steps of the method described in PCT/EP2015/074896, incorporated by reference, published under number WO 2016 066651 (the "final reference model" mentioned in step e) of WO 2016 066651 corresponding to the present "updated reference model").

At step 3), all the statistical analysis methods may be used.

Advantageously, the statistical analysis makes it possible to establish correlations between the historical data, and in particular parameter values of the orthodontic appliance possibly worn and its behavior, without needing to establish analytically each of the correlations.

The statistical analysis is preferably implemented by a computer program.

The statistical analysis includes an analysis of the historical data in order to predict the value of one or more context parameters at a future time point depending on a set of constraints imposed for this prediction, and especially current data.

The statistical analysis makes it possible to predict, at a future time point, preferably any future time point, the value of at least one tooth positioning parameter of the current patient, for example the theoretical position of any point of a tooth.

More precisely, the statistical analysis makes it possible to construct a predictive model from the historical data to predict how the value of certain parameters will evolve according to "input data".

Preferably, the historical data comprise the values of context parameters relating to previous dental situations experienced by the current patient. Preferably, the statistical analysis assigns a weight to these values that is higher than that of values of these context parameters relating to previous dental situations experienced by other patients.

Thus, for example, if the current patient is undergoing orthodontic treatment, the analysis of the historical data from other orthodontic treatments, for example from 1000 other similar orthodontic treatments, may lead to estimating that the movement of the centroid of a patient's tooth along the x-axis in the month following the current time point should be 60 µm. If the analysis of the historical data of just the current patient leads to estimating this movement at 50 µm, the statistical analysis could, for example, estimate this movement at 55 µm. In this example, the weight of the patient's historical data is therefore 1000 times greater than that of the historical data of the other patients.

The input data are values that fix the values of certain parameters.

The values of certain parameters may only be input data. These parameters thus constitute nonadjustable constraints.

For example, the prediction is necessarily made from the position of the tooth of the current patient at the current time point. The values of the tooth positioning parameters of the current patient at the current time point are therefore input data.

Likewise, if the current patient is undergoing an orthodontic treatment, the prediction is made from a current dental situation in which an orthodontic appliance is worn on the teeth in their current position. The value of certain parameters of the orthodontic appliance at the current time point, for example the position of the attachment points, may therefore also be imposed. The class of the current orthodontic appliance or its intrinsic parameters are other examples of nonadjustable parameters.

The parameters that are not nonadjustable constraints may be fixed or be allowed to vary only in fixed ranges. They constitute adjustable constraints, especially by the orthodontist and/or the patient.

For example, the total duration of an orthodontic treatment may be fixed at 6 months. A pain coefficient measuring the maximum pain during an orthodontic treatment may also be fixed.

In a preferred embodiment, the future time point is an "objective" future time point, that is to say corresponding to a predetermined time of the treatment, in particular corresponding to an intermediate or final setup, and a range for the possible values of a tooth positioning parameter is imposed at this future time point. This positioning parameter is then an adjustable constraint.

A parameter is an adjustable constraint only if, for the statistical analysis, it is decided to limit the domain of its possible values. Otherwise, it is a free parameter.

The parameters that are not constraints are therefore free to vary. If the domains of the possible values for the adjustable constraints are sufficiently large and if the adjustable constraints are not too numerous, the statistical analysis will make it possible to predict at least one future dental situation respecting the constraints. Otherwise, simple tests will make it possible to obtain at least one prediction by relaxing certain constraints.

Many parameters may be adjustable constraints. The statistical analysis therefore often makes it possible to determine several "potential orthodontic treatments" to improve the dental situation of the current patient. Simple tests make it possible to limit the ranges of possible values for the adjustable constraints in order to limit the number of potential orthodontic treatments.

Preferably, if the current patient is undergoing an orthodontic treatment, the statistical analysis only uses historical data for dental situations relating to orthodontic appliances of the same class as the current orthodontic appliance. The precision of the prediction is thereby improved.

Preferably, the statistical analysis only uses historical data for dental situations relating to previous patients of the same category as the current patient. The precision of the prediction is thereby improved.

A future time point may notably be after the current time point by more than one week, more than 2 weeks, more than 3 weeks, more than 5 weeks, more than 8 weeks, or more than 10 weeks. The prediction is more precise the closer the future time point considered is to the current time point.

Preferably, a future dental situation is determined for a future time point corresponding to an intermediate or final setup.

When the statistical analysis makes it possible to determine several future dental situations for the same future time point, it selects preferably at least one, preferably two, future dental situations corresponding to extreme dental situations, that is to say to situations corresponding to acceptable limit values, at this future time, for an adjustable constraint. The adjustable constraint may be, in particular, a positioning parameter for a tooth for which the orthodontist and/or the patient have set a range of possible values.

Preferably, at least one future dental situation is determined for several different future time points.

When at least one future dental situation is determined for several different future time points, the different future time points may, in particular, be separated by more than 3 days, more than one week or more than 2 weeks, and/or less than 2 months, or less than one month.

Preferably, at least one of the future time points is an "objective" future time point.

The statistical analysis therefore makes it possible to predict a potential orthodontic treatment up to the objective future time point. By setting the adjustable constraints, it is possible to predict several potential orthodontic treatments and therefore to measure the impact of a choice on the adjustable constraints.

The results of the statistical analysis may be presented in any form.

Preferably, the difference between a future dental situation for a future time point and a prediction of the anticipated dental situation for said future time point is presented at a time point prior to the current time point, for example at the beginning of treatment. This presentation of the difference is particularly useful when the future time point corresponds to an intermediate or final setup.

Preferably, the difference between a potential orthodontic treatment and a corresponding prediction of the anticipated orthodontic treatment is presented at a time point prior to the current time point, for example at the beginning of treatment. This presentation of the difference makes it possible to visualize whether the treatment has been proceeding and will proceed in accordance with the initial prediction.

Preferably, several future dental situations are presented, at different future time points, in a single graphic representation.

Preferably, from the result of the statistical analysis, a graphic representation is established showing a prediction of the evolution over time of at least one context parameter.

The evolution over time may be especially that of:
- a parameter of the current orthodontic appliance; and/or
- a tooth positioning parameter for the current patient, for example the evolution over time of the movement from one point of a tooth; and/or
- a probability that the future dental situation will be achieved at a considered future time point; and/or
- a difference from a dental situation constituting an objective at the future time point considered; and/or
- a predictable cost so that the future dental situation at a considered future time point is achieved; and/or
- a pain coefficient so that the dental situation at a considered future time point is achieved.

The time scale is preferably linear. A graphic representation makes it possible, for example, to immediately perceive the dynamics of the action of the orthodontic appliance. In particular, the observation that the curve of a positioning parameter increases or decreases less quickly as time passes, may be interpreted as meaning that the orthodontic appliance is losing its effectiveness.

Such a curve is particularly simple to understand, which makes it possible for the current patient themselves to use it.

In a preferred embodiment, the graphic representation includes indications on the satisfactory or unsatisfactory nature of said evolution. For example, the curve may change color if the slope is considered abnormal. It is therefore possible to determine, for example, the time from which any delay in treatment adaptation will be detrimental.

Preferably, the graphic representation may be displayed on a cell phone. In particular, it may be seen by the patient. Advantageously, patients may therefore decide themselves, at the most opportune time, to take measures to adjust or change their orthodontic appliance or make an appointment with the orthodontist.

In one embodiment, the number of parameters whose evolution is graphically shown is less than 10, preferably less than 5, preferably less than 4, preferably less than 3, preferably less than 2. In one embodiment, the number of points of the tooth for which the evolution of one or more parameters is graphically shown is less than 10, preferably less than 5, preferably less than 4, preferably less than 3, preferably less than 2. Decision making is thereby facilitated.

Preferably, from the result of the statistical analysis, a report is drawn up providing
- diagnostic information and/or recommendations to apply a new orthodontic treatment to the current patient or change an orthodontic treatment applied to the current patient and/or
- a score representing the efficacy of a treatment applied to the current patient and/or alternative potential orthodontic treatments.

The report may especially specify how to change the tension of the current orthodontic appliance archwire or how to make a new aligner.

Preferably, several potential orthodontic treatments are determined which make it possible, from the current dental situation, to achieve a desired positioning of the teeth, then said potential treatments are presented to the patient and/or to the orthodontist so that they may choose one of said potential orthodontic treatments.

Preferably, the modification of the adjustable constraints is repeated for optimization purposes. At each optimization cycle, one or more of said adjustable constraints are modified, then the future dental situation obtained is evaluated until an optimal dental situation is found regarding an optimization criterion, according to at least one optimization rule, and/or preferably, the potential orthodontic treatment obtained is evaluated until an optimal dental situation is found regarding an optimization criterion, according to at least one optimization rule.

Of course, all known optimization methods may be implemented.

More precisely, to conduct an optimization, certain adjustable constraints are conventionally fixed, others are variable in a range that is fixed.

For the optimization of a future dental situation, the optimization criterion may be, for example, a pain coefficient or a cost associated with this situation.

The optimization objective may be, for example, to minimize the pain coefficient at a future time point. A first statistical analysis is then conducted with a first pain coefficient and the result is examined to see if it is acceptable. If the result is acceptable, the pain coefficient is reduced and the new result is examined to see if it is acceptable. Thus, constraints are modified until the lowest pain coefficient allowing an acceptable result to be obtained is determined.

For optimizing an orthodontic treatment, the optimization criterion may be, for example, a difference from a desired value for a positioning parameter at an objective future time point, for example the end of treatment. The optimization criterion may also be a mean pain coefficient evaluating, on average, the pain until the end of treatment or a total cost of treatment.

At each optimization cycle, it is then necessary to predict a potential orthodontic treatment, to measure the optimization criterion for this potential orthodontic treatment, for example by averaging the pain coefficients associated with each future dental situation of the potential orthodontic treatment, then modifying one or more adjustable constraints while respecting the ranges in which these variable constraints may vary.

By comparing the values of the optimization criterion obtained for the different cycles, the optimal potential orthodontic treatment may thus be sought.

The optimization rule may be, for example, to minimize or maximize the optimization criterion value.

Optimization is preferably carried out by a computer, the orthodontist or the patient only specifying the adjustable constraints, for example a maximum value or acceptable range for the adjustable constraints.

For example, the orthodontist may impose a maximum cost, a maximum duration, a maximum pain coefficient, a maximum number of appointments or a maximum number of aligners. They may also specify, depending on the orthodontic treatment objective, the range of acceptable values for one or more context parameters, and in particular positioning parameters (range P in FIG. 2, described below).

By statistical analysis of the historical data, the computer and/or orthodontist and/or current patient then seek one or preferably several future dental situations and preferably one or preferably several potential orthodontic treatments making it possible to satisfy these adjustable constraints.

In one embodiment, if the adjustable constraints imposed do not make it possible to determine a potential orthodontic treatment respecting these constraints, the orthodontist adjusts them, then repeats the statistical analysis and optimization. They start these operations again until at least one potential orthodontic treatment is found.

For example, if the patient wishes their treatment to last less than 3 months, an adjustable constraint related to pain or cost may be at least partially removed.

To best explore the various treatments possible, it is also possible to remove the constraint relative to one or more tooth positioning parameters at an objective future time point. For example, in FIG. 2a, described below, curve T3 was only able to be created because the constraint according to which, at future objective time point $t_f$, the value of positioning parameter x must be comprised in area P has been removed. In return, this constraint was not removed in the example of FIG. 2c.

Optimization may also be partially manual.

At step 4), the orthodontist analyzes the results obtained at step 3) and optionally determines an orthodontic treatment or modifies a current orthodontic treatment depending on these results and, preferably, depending on the choice of the current patient.

The predictive capacity offered by the invention makes it possible, in particular, to determine an orthodontic treatment according to constraints such as the treatment cost, the number of orthodontist appointments, the shape or adjustment of the orthodontic appliance, pain, treatment duration or the probability of success.

The orthodontist may believe that the situation is acceptable and decide not to implement the orthodontic treatment for the current patient or not to modify an orthodontic treatment that the current patient is undergoing. Alternatively, they may decide to create an orthodontic appliance or modify the current orthodontic appliance possibly worn by the current patient or switch it out.

The orthodontist may, in particular, modify the tension of an orthodontic archwire of the current orthodontic appliance and/or a new orthodontic aligner is created to replace the current orthodontic appliance. In one embodiment, the current orthodontic appliance is an aligner, and the patient is sent a second aligner created according to the results of the statistical analysis of step 3).

The orthodontic appliance is thus well suited to the reality of treatment.

The orthodontist may also advantageously decide to modify the treatment initially envisaged, notably by modifying the intermediate setups.

In the case of an orthodontic treatment by means of aligners, the method makes it possible to limit the number of aligners created. The aligners may, in particular, be created throughout the treatment, which enables them to be perfectly adjusted to the actual situation at the time that they need to be used.

Finally, the cost and duration of treatment are reduced.

EXAMPLES

Figure 2A:
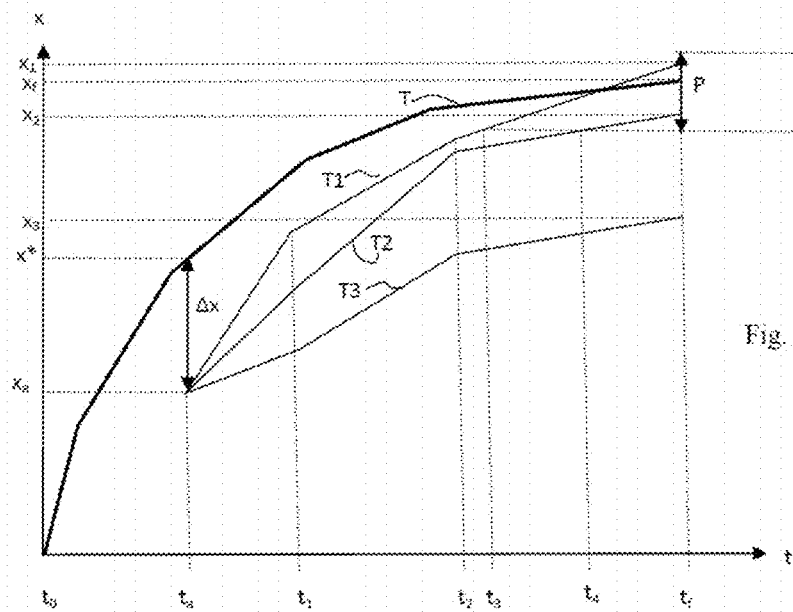

In FIG. 2a, three potential orthodontic treatments are represented, T1, T2 and T3, corresponding to three sets of different constraints. For each potential orthodontic treatment, a future dental situation has been evaluated, by statistical analysis, at time points $t_1$, $T_2$ and $t_f$.

The x-axis provides time. The y-axis provides the value of context parameter x, for example the, position of a point of a tooth according an axis Ox).

Range P is a constraint imposed x at time point $t_f$. It actually specifies the range of acceptable positions for this point, at objective future time point $t_f$ corresponding, for example, to the end of treatment with the current orthodontic appliance. The bounds of this range correspond to extreme dental situations acceptable for the value of x at time point $t_f$.

In a first stage, the orthodontist may choose not to impose range P.

The three potential orthodontic treatments T1, T2 and T3 may for example differ by values for the pain experienced, corresponding for example to three possible settings of the tension of the orthodontic archwire. For example, a pain coefficient measuring the pain experienced may be for example 200, 150 and 100 for the potential orthodontic treatments T1, T2 and T3, respectively.

From current time point $t_a$, the statistical analysis, done for each of future time points $t_1$, $t_2$ and $t_f$ and at each of these future time points for the three pain coefficient values, makes it possible to predict the orthodontic treatment according to the pain coefficient. It is observed for example that if the patient accepts a pain coefficient of 200 (curve T1), the objective for the context parameter considered will be attained at time point $t_3$. It will be attained at time point $t_4$ with the pain coefficient of T2. FIG. 2a shows that the treatment objective will not be attained with the current orthodontic appliance if the current patient wishes to apply the pain coefficient of T3. In agreement with the current patient, the orthodontist may then choose to lengthen the duration of the treatment or to widen range P or to modify the current orthodontic treatment, for example by switching out the current orthodontic appliance, which may result in additional costs.

Curve T in FIG. 2a represents the treatment planned initially, at initial time point $t_0$. At current time point $t_a$, by observing the patient's teeth, a significant difference Δx may be observed between actual position $x_a$ and position x* initially planned at time point $t_a$. Without the prediction according to the invention, the orthodontist would have probably decided to modify the treatment, for example by switching out the orthodontic appliance. If the current orthodontic appliance is the one corresponding to curve T2, they may advantageously observe that the delay will be made up without needing to change the treatment.

Figure 2B:
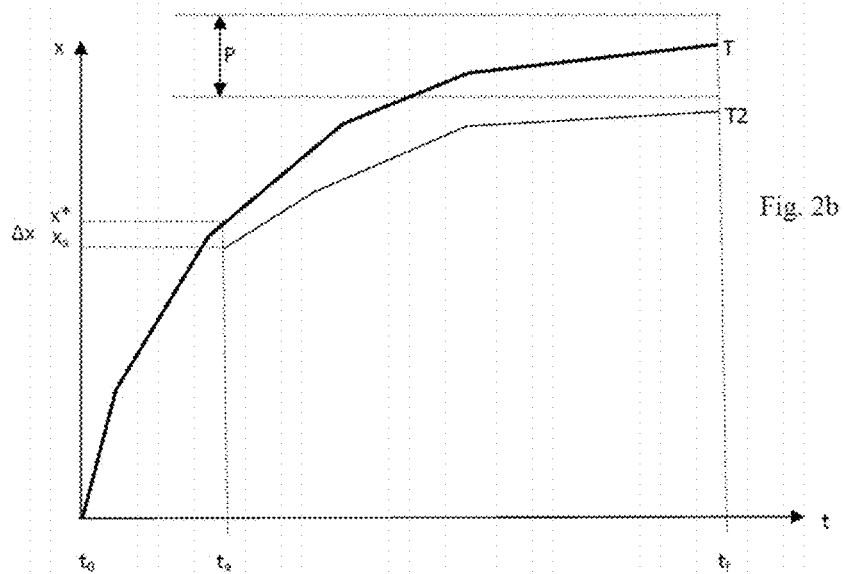
Figure 2C:
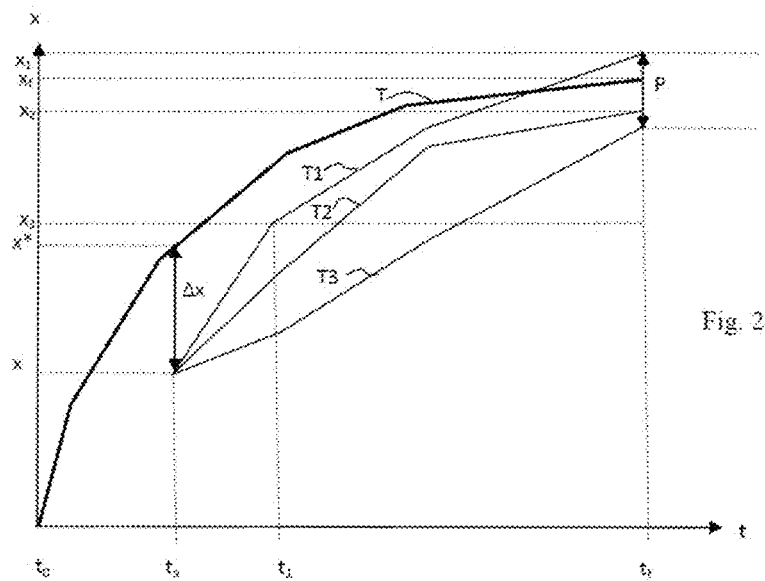

Reciprocally, as shown in FIG. 2b, at current time point $t_a$, by observing the patient's teeth, the orthodontist can observe a slight difference Δx between actual position $x_a$ and position x* initially planned at time point $t_a$. Without the prediction according to the invention, the orthodontist would probably have decided not to modify the treatment. If the current orthodontic appliance is the one corresponding to curve T2, they may advantageously observe that the difference will increase and that the objective will not be attained if the treatment is not modified.

The statistical analysis thus makes it possible to accurately anticipate the behavior of an orthodontic appliance according to the value of its parameters and the configuration of the teeth in which it is placed, but also to simulate alternative treatments, for example by modifying the constraints.

The curves corresponding to potential orthodontic treatments T1, T2 and T3 also make it possible, at each future time point, to visualize the difference between the predicted future dental situation if one of these potential orthodontic treatments is applied and the dental situation constituting the objective at said future time point (curve T). In particular, at time point $t_f$, FIG. 2a makes it possible to visualize the difference between the objective for the context parameter value considered, $x_f$, and the corresponding values $x_1$, $x_2$ and $x_3$ for the future dental situations predicted with the constraints associated with potential orthodontic treatments T1, T2 and T3.

The orthodontist may also decide to impose range P as a constraint to be respected. The optimization then leads to a graphic representation like that of FIG. 2c.

Figure 2D:
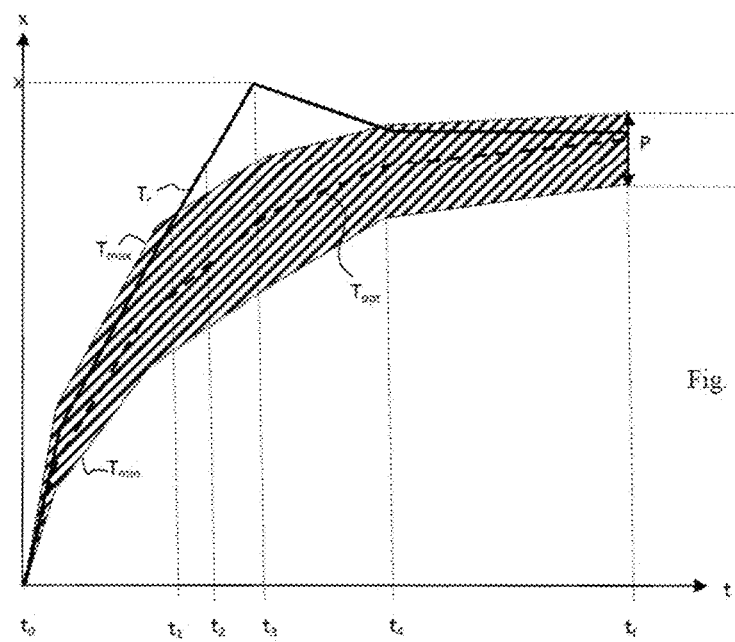
Figure 2E:
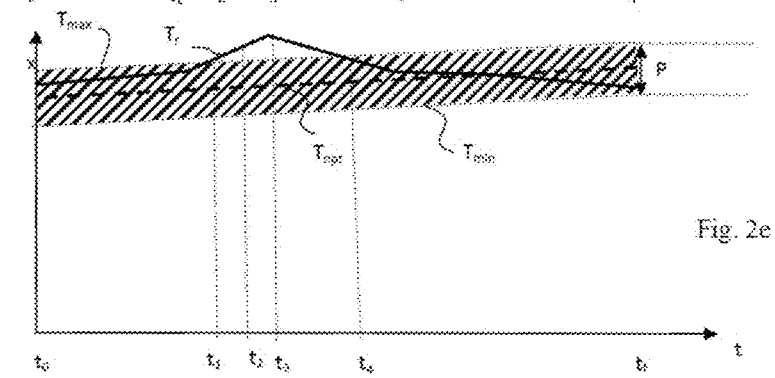

In one embodiment, as represented in FIG. 2d, from initial time point to, for example at the beginning of treatment, a so-called "optimal" potential orthodontic treatment for a parameter, for example a positioning parameter, and extreme potential orthodontic treatments corresponding to minimum and maximum limits considered acceptable for said positioning parameter are determined. These potential orthodontic treatments are represented by the curves $T_{opt}$, $T_{max}$ and $T_{min}$, respectively, in FIG. 2d. Curves $T_{max}$ and $T_{min}$ thus define an envelope providing, at any time point up to objective future time point $t_f$, a tolerance with regard to curve $T_{opt}$ relative to the optimum treatment. At final time point $t_f$, for example at the end of treatment or at an intermediate setup, this tolerance corresponds to the range P of final positions accepted. The area which extends between curves $T_{max}$ and $T_{min}$, hatch-marked in FIGS. 2d and 2e, is called the "biozone".

In FIG. 2d, curve $T_f$ represents the actual evolution of the parameter value considered, in this case position x.

At any time, it is possible, very simply, to check whether position x is in the biozone. If that is the case, the treatment proceeds normally. Otherwise, it is necessary to correct the treatment as a consequence.

In the example of FIG. 2d, position x left the biozone at time point $t_1$, the anomaly was detected at time point $t_2$ and the treatment was modified at time point $t_3$. The modification made it possible to bring curve $T_f$ back into the biozone, from time point $t_4$.

The biozone is particularly a particularly effective tool to quickly check whether a treatment is proceeding as planned.

In the example of FIG. 2e, the method according to the invention is used outside orthodontic treatment, the teeth of the current patient being normally positioned. Optimal curve $T_{opt}$ corresponds to a "normal" evolution for the current patient, who is an elderly person. Curves $T_{max}$ and $T_{min}$ define the envelope of the biozone.

Actual position x is monitored. Each measurement of position x is compared, at the corresponding time point, to the biozone. Position x left the biozone at time point $t_1$, the anomaly was detected at time point $t_2$ and a treatment was applied from time point $t_3$. The modification made it possible to bring curve $T_f$ back into the biozone, from time point $t_4$.

As appears clearly at present, the method according to the invention makes it possible to optimize the orthodontic treatment, while improving the information provided to the patient.

Of course, the invention is not limited to the embodiments described and shown above.

In particular, the patient is not limited to a human being. In particular, a method for controlling the positioning of teeth according to the invention may be used for another animal.

The invention is not limited to the context of an orthodontic treatment applied to the current patient. A prediction of the evolution of the position of the teeth is also possible while the patient is not undergoing any treatment, for example for monitoring purposes.

The invention claimed is:

1. A method for predicting a future dental situation for a patient, called "current patient", said prediction method including the following steps:
1) acquisition of data, called "historical data", relative to more than 1000 past dental situations, called "previous dental situations", each experienced, at a time point called "previous time point", by a patient called "previous patient", all the historical data relative to a previous dental situation including at least:
said previous time point;
context parameter values at said previous time point, the context parameters including tooth positioning parameters of said previous patient;
2) acquisition at a time point, called "current time point", of data relative to a dental situation experienced by said current patient, called "current dental situation", all the data related to said current dental situation, called "current data", including at least:
preferably, said current time point;
context parameter values at said current time point, the context parameters including tooth positioning parameters of said current patient;
3) statistical analysis of said historical data and said current data, so as to determine, for at least one future time point and for at least one future dental situation for the current patient,
if the current patient has a current orthodontic appliance, values, at said future time point, of parameters of said current orthodontic appliance; and/or
values of tooth positioning parameters of said current patient at said future time point; and/or
a difference from a dental situation constituting an objective at said future time point; and/or
a cost for said future dental situation to be achieved; and/or
a pain coefficient for said future dental situation to be achieved; and/or
a probability that the predictions relating to said parameters of said current orthodontic appliance and/or the tooth positioning parameters of said current patient, and/or said cost and/or said pain coefficient will comply with reality;
4) a probability that the predictions relating to said parameters of said current orthodontic appliance and/or the tooth positioning parameters of said current patient, and/or said cost and/or said pain coefficient will comply with reality depending on said future dental situation, evaluation of the benefit of an orthodontic treatment or, if the current patient has an orthodontic appliance, called "current orthodontic appliance", reevaluation of the orthodontic treatment of said current patient and, depending on said reevaluation, possible modification of the orthodontic treatment of the current patient,
method according to which at step 1) or 2), to acquire said historical data and/or said current data, respectively, the following steps are implemented:
a) creating a three-dimensional digital reference model of at least one part of an arch of said previous patient and/or said current patient, respectively, or "initial reference model" and, preferably, for each tooth, defining, from the initial reference model, a three-dimensional digital reference model of said tooth, or "tooth model";
b) acquiring at least one two-dimensional image of the arches of said previous patient and/or said current patient, respectively, called "updated image" under actual acquisition conditions;
c) analysing each updated image and creation, for each updated image, of an updated map relating to discriminant information;
e) searching, for each updated image, by deformation of the initial reference model, for an updated reference model corresponding to the positioning of the teeth during the acquisition of the updated image, the search being preferably carried out by means of a metaheuristic method, preferably an evolutionary method, preferably by simulated annealing, and
f) collecting data relative to the updated reference model and relative to the orthodontic appliance of said previous patient and/or said current patient, respectively.

2. The method as claimed in claim 1, wherein the context parameters at said previous time point include:
if the previous patient has an orthodontic appliance, called "previous orthodontic appliance",
at least one parameter of said previous orthodontic appliance relative to the class and/or conformation of the previous orthodontic appliance; and/or
at least one parameter on the orthodontic treatment environment to which the previous dental situation relates, called "previous orthodontic treatment", chosen from among a pain coefficient, a cost, a duration, a number of orthodontist appointments and a probability of success, associated with said previous orthodontic treatment;
and/or
at least one functional parameter of the previous patient; and/or
at least one anatomical parameter of the previous patient other than the tooth positioning parameters; and/or
the age and/or sex and/or an identifier of said previous patient.

3. The method as claimed in claim 1, wherein the context parameters at said current time point include:
if the current patient has with a current orthodontic appliance,
at least one parameter of said current orthodontic appliance relative to the class and/or conformation of the current orthodontic appliance; and/or
at least one parameter on the current orthodontic treatment environment to which the current dental situation relates, called "current orthodontic treatment", chosen from among a pain coefficient, a cost, a duration, a number of orthodontist appointments and a probability of success, associated with said current orthodontic treatment;
and/or
at least one functional parameter of the current patient; and/or
at least one anatomical parameter of the current patient other than the tooth positioning parameters; and/or
the age and/or sex and/or an identifier of said current patient.

4. The method as claimed in claim 1, wherein, at step 3), several future situations are determined, for a single future time point, and/or at least one future dental situation, for several different future time points.

5. The method as claimed in claim 1, wherein, at step 3), several said statistical analyses are carried out, each time modifying said future time point, so as to predict future dental situations up to a future objective time point, and thus constitute a "potential orthodontic treatment" up to said objective future time point.

6. The method as claimed in claim 5, wherein several potential orthodontic treatments are determined, by changing one constraint each time.

7. The method as claimed in claim 6, wherein first and second potential orthodontic treatments are determined which lead, for at least one tooth positioning parameter of the current patient, to extreme dental situations for said objective future time point, an extreme dental situation corresponding to a minimum or maximum limit for said tooth positioning parameter of said current patient.

8. The method as claimed in claim 7, wherein the evolution over time of the value of said positioning parameter for the first and second potential orthodontic treatments is represented in a single graph.

9. The method as claimed in claim 5, wherein the initial time point of the potential orthodontic treatment or treatments is the current time point or an initial time point corresponding to the start of a current orthodontic treatment with an orthodontic appliance worn by the current patient.

10. The method as claimed in claim 1, including an operation of optimizing constraints depending on at least one optimization criterion, an operation in which a succession of steps 3) are implemented by changing one or more of said constraints each time, until an optimal dental situation is found with regard to an optimization criterion, following at least one optimization rule.

11. The method as claimed in claim 10 wherein the optimization criterion is chosen from the group made up of a pain coefficient, a cost, a difference from a desired value for a positioning parameter, a duration, a number of orthodontist appointments, a number of aligners, a probability of success, or a combination of these criteria, each criterion being able to be associated with the current orthodontic treatment or a dental situation of said current orthodontic treatment.

12. The method as claimed in claim 1, wherein step e) includes the following steps:
   e1) defining a reference model to test as being the initial reference model, then
   e2) following the next steps, testing virtual acquisition conditions with the reference model to test in order to finely approximate said actual acquisition conditions;
   e21) determining virtual acquisition conditions to test;
   e22) creating a two-dimensional reference image of the reference model to test under said virtual acquisition conditions to test;
   e23) processing the reference image to create at least one reference map representing, at least partially, said discriminant information;
   e24) comparing the updated and reference maps so as to determine a value for a first evaluation function, said value for the first evaluation function depending on the differences between said updated and reference maps and corresponding to a decision to continue or to stop the search for virtual acquisition conditions approximating said actual acquisition conditions with more accuracy than said virtual acquisition conditions to test determined at the last occurrence of step e21);
   e25) if said value for the first evaluation function corresponds to a decision to continue said search, modifying the virtual acquisition conditions to test, then resuming at step e22);
   e3) determining a value for a second evaluation function, said value for the second evaluation function depending on the differences between the updated and reference maps under the virtual acquisition conditions best approximating said actual acquisition conditions and resulting from the last occurrence of step e2), said value for the second evaluation function corresponding to a decision to continue or to stop the search for a reference model approximating the positioning of the teeth during the acquisition of the updated image with more accuracy than said reference model to test used at the last occurrence of step e2), and if said value for the second evaluation function corresponds to a decision to continue said search, modifying the reference model to test by moving one or more tooth models, then resuming at step e2).

13. The method as claimed in claim 1, comprising between the step c) and e), the determination for each updated image, of virtual acquisition conditions.

14. A method for predicting a future dental situation for a patient, called "current patient", said prediction method including the following steps:
   1) acquisition of data, called "historical data", relative to more than 1000 past dental situations, called "previous dental situations", each experienced, at a time point called "previous time point", by a patient called "previous patient", all the historical data relative to a previous dental situation including at least:
      said previous time point;
      context parameter values at said previous time point, the context parameters including tooth positioning parameters of said previous patient;
   2) acquisition at a time point, called "current time point", of data relative to a dental situation experienced by said current patient, called "current dental situation", all the data related to said current dental situation, called "current data", including at least:
      preferably, said current time point;
      context parameter values at said current time point, the context parameters including tooth positioning parameters of said current patient;
   3) statistical analysis of said historical data and said current data, so as to determine for at least one future time point and for at least one future dental situation for the current patient,
      if the current patient has a current orthodontic appliance, values, at said future time point, of parameters of said current orthodontic appliance; and/or
      values of tooth positioning parameters of said current patient at said future time point; and/or
      a difference from a dental situation constituting an objective at said future time point; and/or
      a cost for said future dental situation to be achieved; and/or
      a pain coefficient for said future dental situation to be achieved; and/or
      a probability that the predictions relating to said parameters of said current orthodontic appliance and/or the tooth positioning parameters of said current patient, and/or said cost and/or said pain coefficient will comply with reality;
   4) depending on said future dental situation, evaluation of the benefit of an orthodontic treatment or, if the current patient has an orthodontic appliance, called "current orthodontic appliance", reevaluation of the orthodontic treatment of said current patient and, depending on said reevaluation, possible modification of the orthodontic treatment of the current patient.

15. Method for predicting a future dental situation for a patient, called "current patient", said prediction method including the following steps:

1) acquisition of data, called "historical data", relative to more than 1000 past dental situations, called "previous dental situations", each experienced, at a time point called "previous time point", by a patient called "previous patient", all the historical data relative to a previous dental situation including at least:
   said previous time point;
   context parameter values at said previous time point, the context parameters including tooth positioning parameters of said previous patient;
2) acquisition at a time point, called "current time point", of data relative to a dental situation experienced by said current patient, called "current dental situation", all the data related to said current dental situation, called "current data", including at least:
   preferably, said current time point;
   context parameter values at said current time point, the context parameters including tooth positioning parameters of said current patient;
3) statistical analysis of said historical data and said current data, so as to predict, at at least one future time point, at least one future dental situation for the current patient;
4) depending on said future dental situation, evaluation of the benefit of an orthodontic treatment or, if the current patient has an orthodontic appliance, called "current orthodontic appliance", reevaluation of the orthodontic treatment of said current patient and, depending on said reevaluation, possible modification of the orthodontic treatment of the current patient, method wherein at step 3), first and second potential orthodontic treatments are determined by changing one constraint each time, several said statistical analyses being carried out, each time modifying said future time point, so as to predict dental situations up to a future objective time point, and thus constituting a "potential orthodontic treatment" up to said objective future time point, said first and second potential orthodontic treatments being determined to lead, for at least one tooth positioning parameter of the current patient, to extreme dental situations for said objective future time point, an extreme dental situation corresponding to a minimum or maximum limit for said tooth positioning parameter of said current patient.

* * * * *